United States Patent [19]
Chapman

[11] Patent Number: 5,155,256
[45] Date of Patent: Oct. 13, 1992

[54] PROCESS FOR PREPARING 2-BROMOETHYL ACETATE

[75] Inventor: Robert C. Chapman, Manchester, Mo.

[73] Assignee: Mallinckrodt Medical, Inc., St. Louis, Mo.

[21] Appl. No.: 718,624

[22] Filed: Jun. 21, 1991

Related U.S. Application Data

[63] Continuation of Ser. No. 567,004, Aug. 13, 1990, which is a continuation of Ser. No. 179,848, Apr. 11, 1988.

[51] Int. Cl.$^5$ .............................................. C07C 67/02
[52] U.S. Cl. ................................................... 560/266
[58] Field of Search ......................................... 560/266

[56] References Cited

U.S. PATENT DOCUMENTS 2,835,709  5/1958  Mann .................................. 560/266

OTHER PUBLICATIONS

Weygard et al., Preparative Organic Chemistry John Wiley & Sons, N.Y., 1972, pp. 368-369 and 214-215.

*Primary Examiner*—Jose G. Dees
*Assistant Examiner*—Joseph M. Conrad
*Attorney, Agent, or Firm*—Senniger, Powers, Leavitt & Roedel

[57] ABSTRACT

An improved process for preparing 2-bromoethyl acetate involves reacting ethylene glycol with an aqueous solution of hydrogen bromide and acetic acid in the presence of a solvent such as toluene which forms an azeotrope with water but not with 2-bromoethyl acetate. The resulting reaction mixture is heated under reflux conditions to separate toluene and water therefrom and acetic anhydride or acetic acid is added to convert bromoethanol in the reaction mixture to additional 2-bromoethyl acetate.

12 Claims, No Drawings

PROCESS FOR PREPARING 2-BROMOETHYL ACETATE

This is a continuation of application Ser. No. 567,004 filed Aug. 13, 1990, which is a continuation of application Ser. No. 179,848 filed Apr. 11, 1988.

BACKGROUND OF THE INVENTION

This invention relates to the preparation of 2bromoethyl acetate and, more particularly, to an improved process for the preparation of 2-bromoethyl acetate which is more cost effective and which produces this compound in good to excellent yield with excellent purity.

2-Bromoethyl acetate is a compound which is employed in the preparation of 5-[N-(2-acetoxyethyl) acetoxyacetamido]-N,N'-bis(2,3-diacetoxypropyl)-2,4,6triiodoisophthalamide which in turn is an intermediate in the preparation of N,N'-bis(2,3-dihydroxypropyl)-5-[N(2-hydroxyethyl) glycolamido]-2,4,6-triiodoisophthalamide. The latter compound is a nonionic x-ray contrast agent (see Lin U.S. Pat. No. 4,396,598 dated Aug. 2, 1983).

Heretofore, it has been known to prepare 2-bromoalkyl acetates (bromohydrin acetates) from 1,2-diols such as ethylene glycol by reacting the diol with 6 molar hydrogen bromide in acetic acid. Golding et al., J. Chem. Soc. Perkin Trans. I, 1973,1214, Bhat et al. Syn. 142 (1984) and Blomquist et al., J. Am. Chem. Soc. 74, 3636 (1952). This preparation involved the use of anhydrous gaseous hydrogen bromide or a saturated solution of hydrogen bromide in acetic acid and requires removal of the water produced by the reaction.

There has been a need in the art for an improved process for preparing 2-bromoethyl acetate which is more cost effective and produces a product of excellent purity in high yield.

SUMMARY OF THE INVENTION

Among the several objects of the present invention, therefore, may be noted the provision of an improved process for the preparation of 2-bromoethyl acetate; the provision of such a process which is more cost effective and produces a product of good quality; and the provision of such a process which is readily carried out and which facilitates the preparation of a key intermediate in the production of a nonionic x-ray contrast agent. Other objects and features will be in part apparent and in part pointed out hereinafter.

Briefly, the present invention is directed to an improvement in a process for preparing 2-bromoethyl acetate, the improvement comprising reacting ethylene glycol with an aqueous solution of hydrogen bromide and acetic acid in the presence of a solvent such as toluene which forms an azeotrope with water but not with 2-bromoethyl acetate. The improved process of the invention also includes the feature of heating the reaction mixture to remove the azeotrope and adding acetic anhydride or acetic acid to the reaction mixture to convert bromoethanol in the mixture to additional 2-bromoethyl acetate product. A further feature of the improved process includes the addition of an antioxidant and a base with the acetic anhydride or acetic acid added to the reaction mixture before distillation to prevent discoloration and to take up any excess free hydrogen bromide.

DESCRIPTION OF THE PREFERRED EMBODIMENTS

In accordance with the present invention, it has now been found that 2-bromoethyl acetate may be prepared in high yield, good quality and less costly by reacting ethylene glycol with an aqueous solution of hydrogen bromide and acetic acid in the presence of a solvent which forms an azeotrope with water but not with 2-bromoethyl acetate. Considerable cost savings are realized by utilizing an aqueous solution of hydrogen bromide such as a 48% aqueous solution rather than employing anhydrous gaseous hydrogen bromide as has been done in the past. Moreover, it has been found that carrying out the reaction in the presence of a solvent which forms an azeotrope with water but not with 2-bromoethyl acetate greatly facilitates the removal of the water normally generated by the reaction enabling a greater yield of the desired 2-bromoethyl acetate to be realized.

In the practice of the invention, ethylene glycol, acetic acid, an aqueous solution of hydrogen bromide and a solvent such as toluene are combined into a reaction mixture and the reaction mixture is heated under reflux conditions at atmospheric pressure to distill an azeotrope containing water, the solvent and some unreacted acetic acid. Surprisingly, there appears to be substantially no loss of hydrogen bromide from the reaction mixture under these conditions. The distillate obtained separates into a water layer and a solvent layer, both of which contain acetic acid. The process is operated continuously with the solvent layer being continuously fed back or recycled to the reaction mixture and the water formed in the reaction which produces 2-bromoethyl acetate being continuously removed as an azeotrope with the solvent. When the water has been substantially removed from the reaction mixture, the latter contains approximately 90% 2-bromoethyl acetate and approximately 10% bromoethanol which is formed by reaction between hydrogen bromide and ethylene glycol.

In order to convert the bromoethanol into the desired 2-bromoethyl acetate, either acetic acid or acetic anhydride are added to the reaction mixture in an amount necessary to react with all bromoethanol present in the mixture. The use of acetic anhydride is preferred since it performs a dual function, i.e. it reacts with any water present to form acetic acid which in turn reacts with bromoethanol to produce additional 2-bromoethyl acetate. After the addition of acetic acid or acetic anhydride, the reaction mixture is subjected to further heating and distillation of the mixture is continued until all of the azeotrope containing water and the solvent together with excess acetic acid has been removed from the mixture. At this point, essentially all of the reactants including any bromoethanol have been converted to the desired 2-bromoethyl acetate product.

As indicated, an important feature of the improved process of the invention resides in carrying out the reaction in the presence of a solvent which forms an azeotrope with water but not with 2-bromoethyl acetate. Toluene is the preferred solvent of this type because of its ready availability. In lieu of toluene, other solvents which form such an azeotrope include 1,1,2-trichloroethane, 1,1,1-trichloroethane, benzene and methylene chloride, but those skilled in the art will appreciate that still other solvents forming the desired azeotrope may also be employed.

In another aspect of the invention, it has been found advantageous to add an antioxidant and a base to the reaction mixture along with the acetic acid or acetic anhydride added to convert bromoethanol to additional 2-bromoethyl acetate. These materials prevent discoloration of the reaction mixture and the base also acts as an acid scavenger to take up any free excess hydrogen bromide. The preferred antioxidant for use in the practice of the invention is sodium bisulfite, but other antioxidants known to the art such as nitric oxide and benzoquinone may also be employed. The preferred base is sodium carbonate, but any alkali metal carbonate or bicarbonate or comparable weak base may also be used.

An illustrative specific embodiment of the process of the invention may be described as follows. The bottom valve of a clean and dry 30 gallon reactor is closed. Using a vacuum acid/organic respirator, 12.9 kg of acetic acid are transferred to the reactor from a nitrogen flushed, grounded drum. Next 18 kg of toluene is vacuum transferred to the reactor from a grounded drum in a hood and 35 kg of a 48% aqueous solution of hydrogen bromide are slowly vacuum transferred from the hood to the reactor. The reaction mixture is then distilled to a receiver adapted to reflux the upper toluene layer while separating and removing the lower water layer until 8.3 gallons of water have been collected. Five additional kg of acetic acid is added to the reaction mixture by gravity and distillation is continued for two more hours. The system is then changed to total take off on the distillation and the reaction mixture is distilled until all toluene and acetic acid have been removed. The toluene/acetic acid in the receiver is then drained into a grounded, nitrogen flushed drum and used in a subsequent run. The 2-bromoethyl acetate product is then distilled under reduced pressure (boiling point approximately 80° C. at 70 mm).

In lieu of adding the acetic acid in the above-described procedure, the reaction mixture is cooled to 20–30° C. after the initial distillation step and approximately 2.6 kg of acetic anhydride or other amount as needed based on the amount of bromoethanol plus water remaining in the reaction mixture is slowly transferred by vacuum with stirring from a grounded, nitrogen flushed drum to the reactor. The reaction mixture is stirred for 2 hours at 25–35° C., the reaction mixture is resampled and additional acetic anhydride as needed is added to react with all bromoethanol present in the reaction mixture 92 g of sodium bisulfite (NaHSO$_3$) is then charged to the reactor along with an amount of sodium carbonate equal to 92 g plus an amount based on the strong acid value of the reaction mixture. The process then proceeds as described above.

The improved process of the invention thus offers significant advantages for preparing 2-bromoethyl acetate in a practical, cost effective and convenient manner and in good yield and purity.

The following examples illustrate the practice of the invention.

EXAMPLE 1

To a suspension of ethylene glycol (6.2 g, 0.1 mol), acetic acid (6.3 ml, 0.11 mol) and toluene (30 ml) was added a 48% aqueous solution of hydrogen bromide (11.8 ml, 0.105 mol), and the mixture was refluxed under Dean Stark conditions for 6 hr. After 4 hr., approximately 11 ml. of water had been collected and after 6 hr., 12.8 ml. of water had been collected. The distillate was removed and distillation was continued at a temperature of approximately 116° C. until all toluene and unreacted acetic acid had been removed as evidenced by gas chromatography. The product mixture contained 92 area % 2-bromoethyl acetate and 8 area % bromoethanol.

EXAMPLE 2

To a solution of ethylene glycol (56 ml, 1.0 mol) and acetic acid (74 ml, 1.3 mol) in toluene (100 ml) was added a 48% aqueous solution of hydrogen bromide (118 ml, 1.05 mol) and the mixture was refluxed under Dean Stark conditions until 125 ml of water had been collected. At this point, gas chromatography showed that the reaction mixture contained approximately 10% bromoethanol. Additional acetic acid (11.4 ml, 0.2 mol) was added and refluxing was continued for 2 hr. at which time the reaction mixture contained approximately 96.5% 2-bromoethyl acetate and 3.5% bromoethanol. Additional acetic acid (11.4 ml, 0.2 mol) was added and refluxing continued for an additional 2 hr. at which time the reaction mixture contained approximately 3% bromoethanol. After stirring the mixture overnight, approximately 2.4 area % bromoethanol remained.

EXAMPLE 3

A mixture of ethylene glycol (56 ml, 1.0 mol), acetic acid (74.4 ml, 1.3 mol), a 48% aqueous solution of hydrogen bromide (112 ml, 1.0 mol) and toluene (100 ml) was heated under reflux under Dean Stark conditions until 128 ml of water had been collected. The water which separated from the distillate contained 13 wt% of acetic acid. More acetic acid (11.4 ml, 0.2 mol) was added and the refluxing continued at a temperature of 106° C. Another portion of acetic acid (11.4 ml, 0.2 mol) was added. A total of approximately 133 ml of water was collected. The material was distilled under 20 mm pressure to remove excess acetic acid and toluene. The pot residue after distilling at head temperatures up to 62° C. at 20 mm contained 122.6g (73.4% yield) of 2-bromoethyl acetate which contained 4 area % bromoethanol.

EXAMPLE 4

To a 4-necked flask were added ethylene glycol (279 ml, 310 g, 5 mol), acetic acid (372 ml, 290 g, 6.5 mol), toluene (500 ml) and an aqueous 48% solution of hydrogen bromide (562 ml, 5 mol) with stirring. The mixture was refluxed under Dean Stark conditions until 665 ml of a water layer had been collected. To this mixture was added acetic anhydride (23.5 ml, 0.25 mol) and the mixture was heated for approximately 25 more minutes. Some bromine evolution was noted. With the reaction mixture at 120°, there was some darkening of the solution. Gas chromatography showed that the reaction mixture contained approximately 4.5% bromoethanol. The reaction mixture was cooled and additional acetic anhydride (23.5 ml, 0.25 mol) was added. After additional heating, gas chromatography showed that the mixture now contained approximately 2.8% bromoethanol.

EXAMPLE 5

To a 3 liter, 4-necked flask fitted with a mechanical stirrer was gradually added ethylene glycol (279 ml, 5 mol), acetic acid (372 ml, 6.5 mol), toluene (400 ml) and an aqueous 48% hydrogen bromide solution (562 mol, 5 mol). The mixture was refluxed under Dean Stark conditions until 750 ml. of a bottom layer of distillate containing water was collected. The mixture was cooled to 25–30°. Gas chromatography showed 14% bromoethanol. The reaction mixture also contained 8.9 g water (0.5 mol). Enough acetic anhydride (113 ml, 1.2 mol) was added to react with residual water and bromoethanol. During the addition, the temperature rose to approximately 50° C., then cooled to 30° C. Gas chromatography showed that the mixture contained less than 0.2% bromoethanol. The material was divided into aliquots.

The solvent was distilled from one aliquot after the addition of 0.1 g of sodium bisulfite to the mixture. The distillate was colorless.

Upon distillation of another aliquot with nothing added, the material darkened.

To the crude mixture (50 ml, 60 g) produced above before dividing into aliquots was added 0.1 g sodium bisulfite and 0.18 g sodium carbonate and the mixture was distilled at 100 mm. pressure until the head temperature stabilized. Very little color formation was noted.

EXAMPLE 6

To a 30 gal reactor was added ethylene glycol (12.9 kg, 208 mol) followed by glacial acetic acid (16.2 kg, 270 mol). The agitator was started and toluene (33 kg) was added. To this mixture at 20° C. was charged an aqueous 48% hydrogen bromide solution (35 kg, 208 mol) and the reaction mixture was heated under reflux conditions for about 2 hr followed by partial reflux conditions from a receiver adapted to reflux the upper toluene layer while allowing collection of the lower water layer. This procedure was continued until 7 and $\frac{3}{4}$ gallons of the lower layer had been collected. The reaction mixture was sampled and the water and bromoethanol levels were measured. The batch was determined to contain 28 mol water and 41 mol bromoethanol. The reaction mixture was cooled to room temperature and acetic anhydride (7.0 kg, 69 mol) was added slowly with stirring and water cooling. The mixture was allowed to stand overnight at room temperature. The excess acetic acid and toluene were then removed by vacuum distillation at 25 mm to a maximum pot temperature of 76° C. The material in the pot was cooled and filtered through a 10 micron filter giving 32.2 kg of 2-bromoethyl acetate. Assay = 95.5%; yield = 92.8%.

EXAMPLE 7

To a 30 gal reactor was charged ethylene glycol (12.9 kg, 208 mol) followed by addition with stirring of glacial acetic acid (16.3 kg, 271 mol), toluene (25.5 kg) and an aqueous 48% hydrogen bromide solution (35.0 kg, 208 mol). The mixture was heated and distilled with partial reflux of the upper toluene layer as described above until approximately 7.5 gal water had been collected and the pot temperature reached 119° C. The mixture was cooled and a sample was analyzed for bromoethanol (25 moles) and water (17 moles) content. Acetic anhydride (4.3 kg, 42 moles) was added slowly to the reaction mixture and it was stirred an additional hour at 28° C. To the reaction mixture were added sodium bisulfite (92 g) and sodium carbonate (141 g) and the mixture was allowed to stand overnight at ambient temperature. The excess toluene and acetic acid were removed under reduced pressure (29.5 in, pot temp. to 84° C.). The 2-bromoethyl acetate which remained in the pot was cooled to room temperature and filtered through a 10 micron filter yielding 33.2 kg product. Yield = 95.7%; Assay = 101%.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. In a process for preparing 2-bromoethyl acetate by reacting ethylene glycol, hydrogen bromide and acetic acid, the improvement comprising reacting under reflux conditions at atmospheric pressure ethylene glycol with an aqueous solution of hydrogen bromide and acetic acid in the presence of a solvent which forms an azeotrope with water but not with 2-bromoethyl acetate, the reactants being present in substantially molar equivalents.

2. An improved process as set forth in claim 1 wherein said solvent is selected from the group consisting of toluene, 1,1,2-trichloroethane, 1,1,1-trichloroethane, benzene and methylene chloride.

3. An improved process as set forth in claim 1 wherein said solvent is toluene.

4. An improved process as set forth in claim 1 wherein said aqueous solution of hydrogen bromide is a 48% aqueous solution.

5. The process for preparing 2-bromoethyl acetate which comprises reacting under reflux conditions at atmospheric pressure ethylene glycol with an aqueous solution of hydrogen bromide and acetic acid in the presence of a solvent which forms an azeotrope with water but not with 2-bromoethyl acetate, the reactants being present in substantially molar equivalents, and thereafter removing water from the reaction mixture containing said 2-bromoethyl acetate.

6. An improved process as set forth in claim 5 wherein said solvent is selected from the group consisting of toluene, 1,1,2-trichloroethane, 1,1,1-trichloroethane, benzene and methylene chloride.

7. An improved process as set forth in claim 5 wherein said solvent is toluene.

8. An improved process as set forth in claim 5 wherein the reaction mixture is heated to remove said solvent and water therefrom.

9. An improved process as set forth in claim 8 wherein a compound selected from the group consisting of acetic anhydride and acetic acid is subsequently added to the reaction mixture to convert bromoethanol in said mixture to additional 2-bromoethyl acetate and remove residual water.

10. An improved process as set forth in claim 9 wherein an antioxidant selected from the group consisting of sodium bisulfite, nitric oxide and benzoquinone and a base selected from the group consisting of alkali metal carbonates and bicarbonates are added to said reaction mixture with said compound selected from the group consisting of acetic anhydride and acetic acid.

11. An improved process as set forth in claim 10 wherein said compound is acetic anhydride, said antioxidant is sodium bisulfite and said base is sodium carbonate.

12. The process for preparing 2-bromoethyl acetate which comprises reacting ethylene glycol with an aqueous solution of hydrogen bromide and acetic acid in the presence of toluene, the reactants being present in substantially molar equivalents, heating the resulting reaction mixture under reflux conditions to separate toluene and water therefrom, adding acetic anhydride to the reaction mixture to convert bromoethanol therein to additional 2-bromoethyl acetate, and distilling the resulting mixture to remove toluene, water and any remaining acetic acid therefrom thereby producing 2-bromoethyl acetate.

* * * * *